United States Patent
Meinhart et al.

(10) Patent No.: US 7,057,198 B2
(45) Date of Patent: Jun. 6, 2006

(54) DEPTH-OF-FIELD MICRON RESOLUTION VELOCIMETRY WITH PULSED IMAGES OF INJECTED SOLID PARTICLES

(76) Inventors: Carl D. Meinhart, 818 Via Campobello, Santa Barbara, CA (US) 93111; Juan G. Santiago, 714 Alvarado Row, Stanford, CA (US) 94305; Ronald J. Adrian, 3418 E. June Cir., Mesa, AZ (US) 85213; Steve T. Wereley, 716 Carrolton Blvd., West Lafayette, IN (US) 47906

( * ) Notice: Subject to any disclaimer, the term of this patent is extended or adjusted under 35 U.S.C. 154(b) by 0 days.

(21) Appl. No.: 10/713,672

(22) Filed: Nov. 13, 2003

(65) Prior Publication Data

US 2006/0049369 A1    Mar. 9, 2006

Related U.S. Application Data

(63) Continuation of application No. 09/453,138, filed on Dec. 2, 1999, now Pat. No. 6,653,651.

(60) Provisional application No. 60/111,514, filed on Dec. 9, 1998.

(51) Int. Cl.
*G01N 15/06* (2006.01)
(52) U.S. Cl. .................................. 250/573; 356/28
(58) Field of Classification Search ........ 250/573–577, 250/356.2; 356/28
See application file for complete search history.

(56) References Cited

U.S. PATENT DOCUMENTS 5,333,044 A    7/1994  Shaffer
5,594,544 A *  1/1997  Horiuchi et al. ............... 356/73

OTHER PUBLICATIONS

J.A. Taylor & E.S. Yeung, "Imaging of Hydrodynamic and Electrokinetic Flow Profiles in Capillaries" Ames Laboratory—USDOE & Dept. of Chemistry, Iowa State University, Ames, Iowa 50011 Analytical Chemistry, 1993.
P.H. Paul, M.G. Garguilo, D.J. Rakestraw, "Imaging of Pressure- and Electrokinetically-driven Flows Through Open Capillaries" Sandia National Laboratories Livermore, CA 1997 Submission to Analytical Chemistry.

* cited by examiner

Primary Examiner—Thanh X. Luu
(74) Attorney, Agent, or Firm—Gene W. Arant (57) ABSTRACT

Method and apparatus for measuring fluid motion with micron scale spatial resolution, in which fluorescent particles are injected into a fluid body in a test device, the test device is broadly illuminated with pulses of light at the excitation frequency of the fluorescent particles, the fluorescent light is collected by a microscope objective lens, and the light thus collected is relayed through a fluorescent filter to an image recording device, the depth of field of the objective lens defining the thickness of a two-dimensional measurement plane.

26 Claims, 12 Drawing Sheets

DEPTH-OF-FIELD MICRON RESOLUTION VELOCIMETRY WITH PULSED IMAGES OF INJECTED SOLID PARTICLES

PRIORITY CLAIMS

This application claims the priority of Ser. No. 09/453,138 filed Dec. 2, 1999; now issued U.S. Pat. No. 6,653,651; and Provisional Patent Application Ser. No. 60/111,514, filed Dec. 9, 1998.

BACKGROUND

1. Field of Invention

This invention relates to instrumentation for measuring fluid motion, specifically the measurement of fluid motion at multiple points.

2. Discussion of Prior Art

Particle Image Velocimetry (PIV) is a technique in which one can measure the velocity of the flow at many, often thousands, of points in the flow simultaneously. Accurate velocity measurements of fluid motion using Particle Image Velocimetry (PIV) are typically on the order of 1 mm (see U.S. Pat. No. 5,333,044 to Shaffer, 1994, U.S. Pat. No. 1991000671529 to Komerath, 1991, U.S. Pat. No. 5,708,495 to Pitz, 1998, U.S. Pat. No. 5,979,245 to Hirano et al. 1999, Northrup, et al., 1991, and a review by Adrian, 1991).

U.S. Pat. No. 5,333,044 to Shaffer, 1994, claims a method for using fluorescent particle images to measure velocity of a flowing fluid close to solid surfaces. According to Shaffer, 1994, an optical apparatus is used to deliver a sheet of light to excite fluorescently-dyed particles in a flowing fluid (see FIGS. 2 & 3 of Shaffer, 1994). The two-dimensional measurement plane is defined by a sheet of illuminating laser light, following common practice in the art of Particle Image Velocimetry. Furthermore, in the invention of Shaffer (1994), the sheet of illuminating light is delivered by an optical apparatus separate from the optical apparatus that receives the fluorescent light and images the fluorescent light onto the image recording device (i.e. the CCD camera). In most practical applications of micron-resolution PIV, optical access is very limited, and it most practical applications of micron-resolution PIV, optical access is very limited, and it is necessary to use the same optical apparatus both to deliver the illumination light and to receive the filtered fluorescent light from the particles. This is not possible with the invention described by Shaffer (1994).

The PIV technique was extended by Urushihara, et al. (1993) and then by Keane et al. (1995) to obtain velocity measurements with spatial resolutions on the order of 100–200 microns.

The first attempt at micron resolution velocimetry was conducted by Brody et al. (1996). They estimated velocity by measuring the image streaks of 0.7 micron diameter particles through a microscope. The resulting velocity measurements were sparse, randomly spaced, low quality, and only accurate to within about 30% full scale. In addition this technique was limited to relatively low velocities.

Lanzillotto et al. (1996) used an X-ray micron-imaging technique to image 1–20 micron diameter emulsion droplets flowing in water. The technique requires a synchrotron to generate the X-rays. We estimate the spatial resolution of this technique to be about 40–100 microns. The accuracy of the technique is limited because of noise in the image field, the size of the emulsion droplets (1–20 microns), and the dispersion of the emulsion droplets relative to the working fluid.

Paul et al. (1997) used a technique related to PIV to analyze to motion of fluorescent dye. We approximate the spatial resolution of this experiment to be on the order of 100 µm×20 µm×20 µm, based on the displacement of the fluorescent dye between exposures, and the thickness of the light sheet used to uncage the fluorescent dye. This technique can be used to measure only one component of velocity with reasonable accuracy.

Hitt, Lowe & Newcomer (1996) used a technique related to PIV, known at Optical Flow, to measure in vivo blood flow in microvascular networks. They used seed particles with diameters on the order of 10 microns. Their measurements were noisy and have low accuracy. We estimate the spatial resolution of this technique to be at best 20 microns in each dimension.

Laser Doppler Velocimetry (LDV) has been a standard technique in fluid mechanics more than 25 years. However, LDV systems can only measure velocities at single points. The spatial resolution of LDV systems is usually on the order of a few millimeters. However, there have been several attempts to increase the spatial resolution to a few microns. Compton & Eaton (1996) used short focal length optics to obtain measurements with spatial resolutions of 35 microns× 66 microns. Tieu, Machenzie, & Li (1995) built a dual-beam solid-state LDA system that had a measurement volume of approximately 5 µm×10 µm. Gharib, Modares & Taugwalder (1998) have developed a Miniature Laser Doppler Anemometer (MLDA), which can be designed to have a measurement diameter (spatial resolution) as small as 10 microns. These LDV systems are limited because they all measure velocity at only a single point.

The Optical Doppler Tomography (ODT) system developed by Chen et al. (1997) uses 1.7 micron diameter particles to measure velocity with a lateral and longitudinal spatial resolution of 5 microns and 15 microns, respectively. The system is noisy and is limited (like LDV) to pointwise measurements.Objects and Advantages Accordingly, several objects and advantages of the current invention are:

(a) to measure flow velocity with higher spatial resolution than other Particle Image Velocimetry (PIV) techniques;

(b) to measure flow velocity at many (often hundreds to thousands) points simultaneously throughout the flow field;

(c) to measure flow velocity at regularly spaced grid points simultaneously throughout the flow field;

(d) to measure flow velocity with low noise and high accuracy;

(e) to measure flow velocity accurately very close to surfaces;

(f) to measure flow velocity over a large range of magnitudes;

(g) to measure flow velocity with high temporal resolution.

Additional objects and advantages are:

(a) to measure instantaneous structures in the flow field, including but not limited to air bubbles and meniscus shapes and positions in liquid flows;

(b) to measure high resolution velocity fields without using fluorescent particles;

(c) the ability to measure flow inside non-transparent devices;

Further objects and advantages will become apparent from a consideration of the drawings and ensuing description.

SUMMARY

This invention is a micron resolution particle image velocimetry (PIV) technique for measuring velocity fields in a fluid flow with spatial resolutions higher than were previously possible. Velocity can be measured at many (often hundreds or thousands) points simultaneously in the flow, and on regularly spaced grid points. The technique can be used to measure a large range of velocity magnitudes.

Figure 1A:
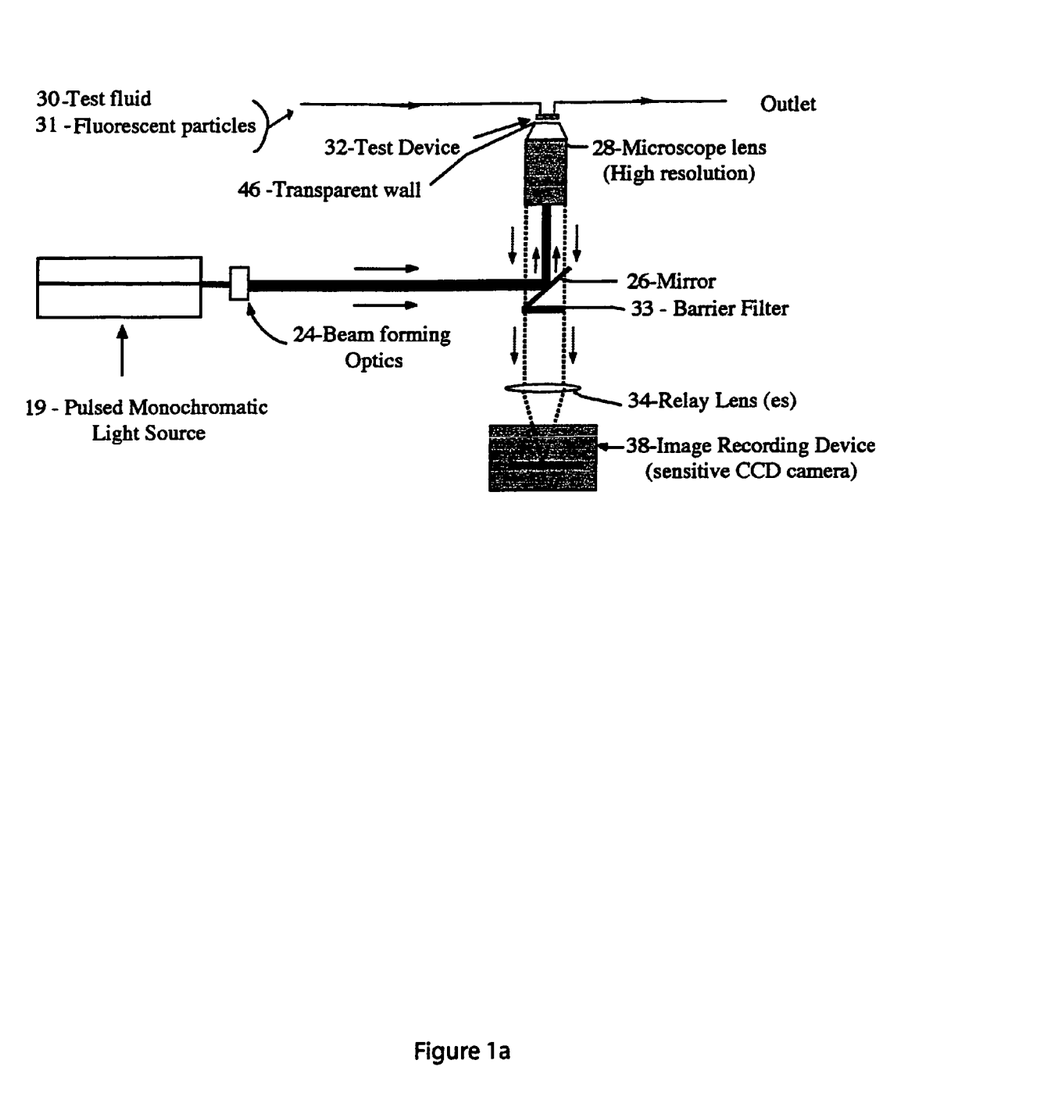
FIG. 1A. Schematic of a micro PIV system using a pulsed monochromatic light. The pulsed monochromatic light source is used to control the particle image field exposure.
Figure 1B:
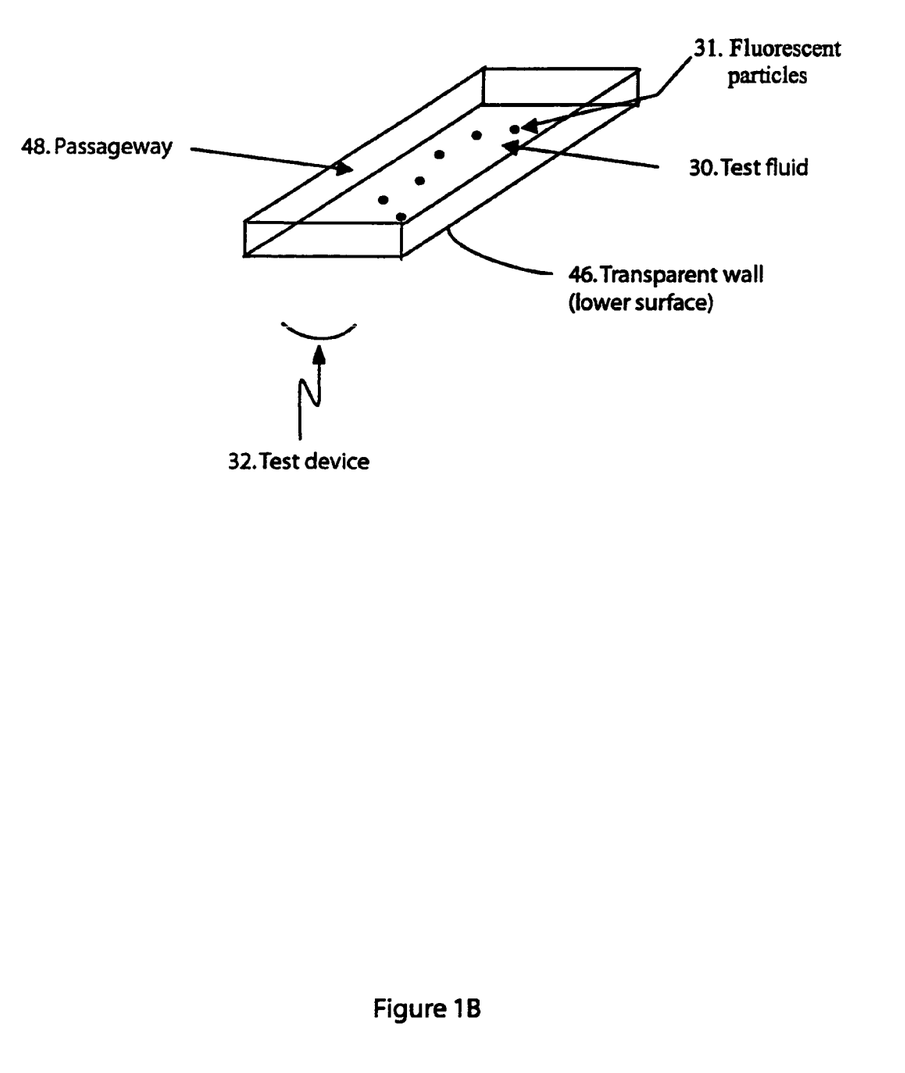
FIG. 1B. Detailed view of test device 32 showing passageway 48 through which test fluid 30 and particles 31 may flow. Transparent wall 46 allows light to pass into and out of the device.

FIGS. 1A & 1B—Description of the Pulsed Monochromatic Light Source System

FIG. 1A is a schematic of the first embodiment of the micron-resolution PIV system. Details of this embodiment are to be published in the journal *Experiments in Fluids*, Meinhart, Wereley & Santiago (1999a). In its first embodiment, the system incorporates a pulsed monochromatic light source 19 (FIG. 1A). Beam-forming optics 24 are located between the pulsed light source 20 and a mirror 26. Above the mirror 26 is a high-resolution microscope lens 28. Test device 32 contains a working fluid 30 with fluorescent flow tracing particles 31. An optical barrier filter 33 is located below the mirror 26. A relay lens(es) 34 is located between an image recording device 38 and the barrier filter 33.

In the preferred embodiment (FIG. 1A), pulsed light source 19 may consist of a pulsed Nd:YAG laser system, available from NewWave Research, Inc., 47613 Warm Springs Blvd., Fremont, Calif. 94539. The laser system is specifically designed for PIV applications, and consists of two Nd:YAG laser cavities, beam combining optics, and a frequency doubling crystal.

Beam-forming optics 24 can consist of a variety of optical elements that will sufficiently modify the light beam so that the light beam from the pulsed monochromatic light source 19 will broadly illuminate test device 32. In the present embodiment, mirror 26 is (R532/T560) antireflective coated (designed to reflect wavelength 532 nm and transmit 560 nm), available from A.G. Heinze, Inc., Three Watson, Irvine, Calif. 92718-2767.

In the preferred embodiment, microscope lens 28 is an oil immersion, high numerical aperture (NA=1.4), high magnification (M=60), low distortion, CFI Plan Apochromat lens manufactured by Nikon, Inc., which is available from A.G. Heinze, Inc., Three Watson, Irvine, Calif. 92718-2767. Lower resolution and lower magnification microscope lenses, such as an air immersion lens with a numerical aperture NA=0.6 and magnification M=40, can be used, but with decreased measurement resolution.

Test fluid 30 can consist of any visibly transparent fluid, such as water. Liquids are most commonly used, but it is conceivable to use gaseous fluids, such as air. The test fluid contains fluorescent particles 31, which can be manufactured from of a variety of materials, such as polystyrene. It is preferred that the particles 31 have a specific gravity closely matched to the test fluid 30, and less than one micron, preferably 200–700 nm. Larger particles can be used, but with decreased performance of the PIV system. The particles must be coated with a fluorescent dye with an excitation wavelength closely matched to pulsed light source 19, and an emission wavelength closely matched to barrier filter 33. Suitable particles can be purchased from Molecular Probes, Inc., 4849 Pitchford Ave., Eugene, Oreg. 97402-0469.

FIG. 1B shows details of test device 32. The test device consists of passageway 48, transparent wall 46 (on at least one surface), and may contain test fluid 30 and fluorescent particles 31. Test device 32 can be any device with one optically transparent wall, so that it can be viewed using microscope lens 28. The test device can range in size from a 1-micron wide microchannel to as large as a 1-m wide wind tunnel. The invention is used to measure flows inside a variety of well known test devices, these include but are not limited to, two microscope coverslips or microscope slides, silicon-micromachined devices (i.e. Micro-Electro Mechanical Systems, MEMS) with a transparent surface, or even flow over a single thin optically transparent surface.

Barrier filter 33 is positioned between the mirror 26 and the relay lens 34. In the current embodiment, barrier filter 33 is a long pass 550 nm filter, available from A.G. Heinze, Inc., Three Watson, Irvine, Calif. 92718-2767.

The relay lens 34 is located next to image recording device 38. The relay lens is a standard part of any video microscope system, available from A.G. Heinze, Inc., Three Watson, Irvine, Calif. 92718-2767.

Image recording device 38 can be a photographic or electronic device that is sensitive enough to record weak fluorescent signals. In the current embodiment, image recording device 38 is a sensitive, cooled, interline-transfer CCD camera, with 1300×1030 pixels. Each pixel is 6.8×6.8 microns, and has 12 bit resolution. This type of CCD camera is available from several camera supply companies, including, Roper Scientific (formerly Princeton Instruments), 3660 Quakerbridge Rd., Trenton, N.J. 08619.

Operation of the Pulsed Light Source System

In the preferred embodiment (FIG. 1A), pulsed light source 19 consists of a pulsed Nd:YAG laser system manufactured specifically for PIV. The laser system produces two light pulses of 5-ns duration, which are separated by a known time delay, ranging from several nanoseconds to several seconds. The first pulse of light is modified by beam forming optics 24, and is reflected by mirror 26 towards microscope lens 28. The microscope lens relays the light so as to broadly illuminate test device 32.

When test fluid 30 and fluorescent particles 31 are located inside test device 32, the particle's fluorescent dye absorbs the original light pulse (wavelength 532 nm, for the preferred embodiment) and emits fluorescent light at a longer wavelength (wavelength ~560 nm, for the preferred embodiment). The emitted light (560 nm) from the fluorescent particles is imaged by microscope lens 28 and passed through mirror 26 to barrier filter 33. Mirror 26 is coated so that it reflects light at wavelength 532 nm and transmits light at wavelength 560 nm. Barrier filter 33 passes light with wavelengths greater than 550 nm, which results from the fluorescence of the particles, and thereby filters out the original pulse of light with a wavelength of 532 nm that is produced by the Nd:YAG laser and reflected by test device 32. Relay lens 34 relays the thus-received and filtered fluorescent light forming an image on the sensor of image recording device 38.

For the preferred embodiment, the image recording device is a CCD camera cooled to −15° C., and has an interline-transfer feature which allows the sensor to can capture two back-to-back image frames with a time delay of several seconds to as short as 500-ns. The cooled sensor allows the camera to record the weak fluorescent signals from the sub-micron particles. After the first set of fluorescent particle images are recorded on the CCD camera, which takes about 10 ns, the image data is transferred to a storage buffer on the CCD camera sensor, which takes about 500 ns. After a known time delay, a second light pulse is emitted by the pulsed light source, and a second set of fluorescent particle images are recorded by the CCD sensor. If test fluid 30 is flowing through passageway 48, fluorescent particles 31 may follow the flow and thereby move a small amount during the known time delay. The relative positions of the particles at each of the two exposures indicate the local displacement of the fluid and subsequently the local velocity. Both sets of fluorescent particle image data are then downloaded to a computer for analysis. Standard PIV analysis algorithms can then be used to measure the velocity at a plurality of points located in the image field. It is common practice to partition the image field into many sub-regions (known as 'interrogation spots') and statistically correlate each sub-region to determine the two-dimensional flow field.

The time duration between successive image exposures determines the temporal resolution of the system (i.e. the averaging time required to obtain a measurement). Using this definition, the temporal resolution limit of the current embodiment is 500 ns for recording particle image exposures on two separate image frames, and approximately 30 ns for recording two particle image exposures on the same image frame.

Standard PIV systems use a light sheet to illuminate the flow-tracing particles in the test device, and therefore the thickness of the light sheet defines the out of plane measurement domain. In the current invention, the entire test device is broadly illuminated, and therefore the out of plane measurement domain must be limited by the depth of field of the objective lens. One criterion for determining the out of plane measurement domain is to determine the distance along the optical axis where a particle becomes sufficiently unfocused so that it only contributes a small fraction, say $\frac{1}{10}^{th}$, to the correlation function, compared to a similar particle that is located at the object plane. Another criterion is to estimate the out of plane measurement domain by focusing the objective lens on a set of particles fixed to a microscope slide, and recording a series of images with the objective lens placed at different axial positions. The out of plane measurement domain can then be estimated by determining the distance the object plane moved to produce sufficiently out of focus particle images, which do not significantly contribute to particle-image correlation.

Analysis of the two sets of particle images is accomplished using the average-correlation algorithm published and described in detail by Meinhart, Wereley & Santiago (1999b). Estimation of velocity-vector fields using PIV involves three primary steps:
1. Particle Image Acquisition
2. Particle Image Correlation
3. Correlation Peak Detection In order to obtain an average velocity measurement, one must apply an averaging operator. The averaging operator is a linear operator, and can be applied after step (1), step (2), or step (3), to produce a non-biased estimate of average velocity. The particle-image correlation and peak detection operations are both nonlinear, and the order in which the averaging operator is applied can dramatically change the quality of the resulting signal.

In the average correlation algorithm the particle-image fields are analyzed to estimate velocity vectors at a single measurement points by (1) cross correlating particle-image fields from several (perhaps 20) instantaneous realizations, (2) ensemble averaging the cross correlation functions, and (3) determining the peak of the ensemble-averaged correlation function. This process is repeated for each velocity-vector location in the measurement domain. The signal-to-noise ratio is significantly increased by averaging the correlation function before peak detection, as opposed to either averaging the velocity vectors after peak detection, or averaging the particle-image field before correlation. This allows one to take maximum advantage of the particle-image data. However, the average correlation technique is usually limited to steady or periodic flows.

Other well-known standard PIV image analysis algorithms can be used to analyze the particle-image fields, but with reduced system performance. Standard PIV algorithms can be commercially purchased from a variety of companies such as TSI, Inc., P.O. Box 64394, St. Paul, Minn., 55164. However, for best system performance, we prefer to use the average correlation algorithm published by Meinhart, Wereley & Santiago (1999b).

For optimal system performance, it is important to choose the proper size and concentration of particles for the flow. The particles must be chosen small enough to follow the flow faithfully without (1) disrupting the flow field, (2) clogging the microdevice, and (3) producing unnecessarily large images. At the same time, the particles must be chosen large enough so that they scatter sufficient light to be recorded, and sufficiently dampen out Brownian motion. Particles ranging in size from 200–700 nm diameter are sufficient for most applications requiring 1–10 micron spatial resolution. Particles larger than 1 micron may be used, but are not recommended because they will substantially reduce the accuracy and spatial resolution of the measurements (Meinhart, Wereley & Santiago, 1999a). The particle concentration must be chosen so that there are not too many particles out of focus particles that will create noise in the image. There must be enough particles to create sufficient signal for the desired spatial resolution. We suggest a particle concentration based on volume of 0.02–0.05%.

Figure 1C:
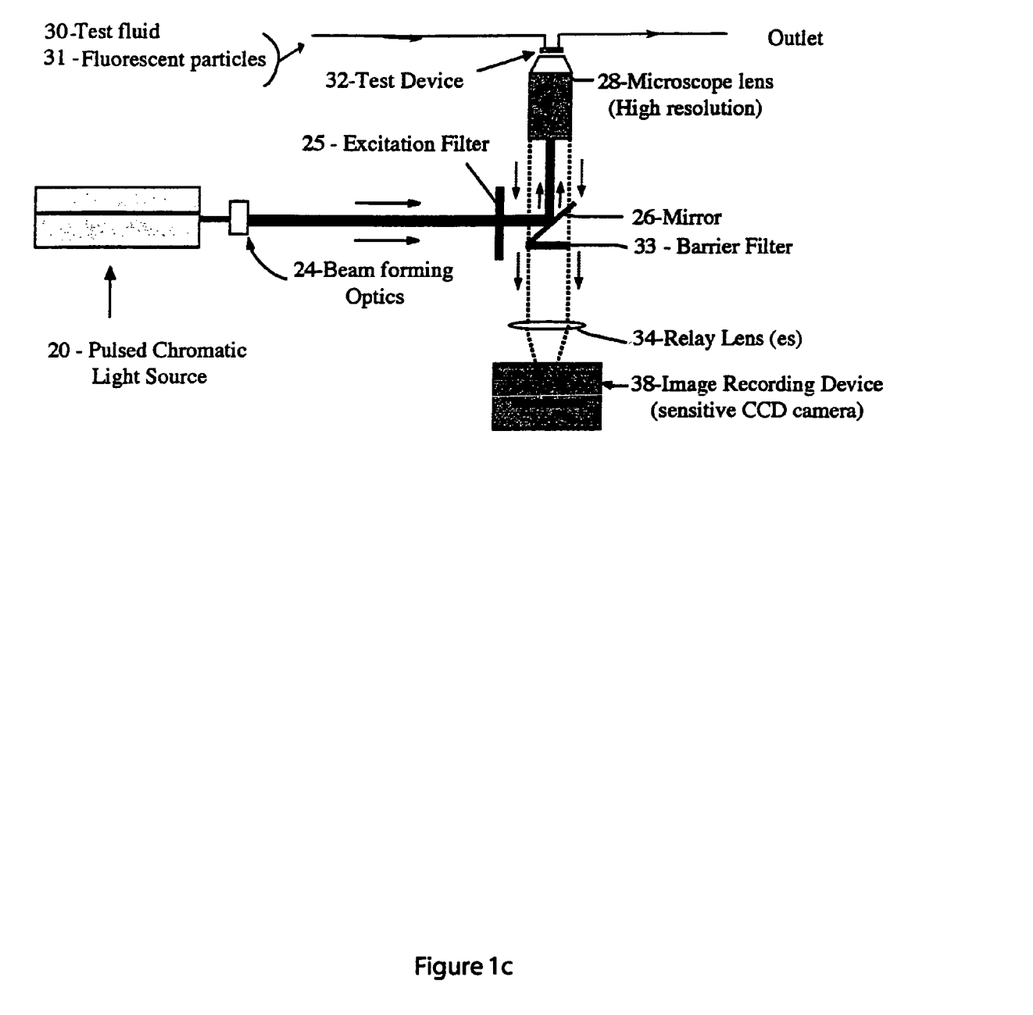
FIG. 1C. Schematic of a micro PIV system using a pulsed chromatic light source. The pulsed light source is used to control the particle image field exposure.

FIG. 1C—Description of Pulsed Chromatic Light Source System

FIG. 1C shows a variation of FIG. 1A, where the pulsed monochromatic light source 19 is replaced by a pulsed chromatic light source 20, such as a strobe lamp available from many laboratory supply companies. An excitation filter 25 is located between beam forming optics 24 and mirror 26. Excitation filters can be purchased from from A.G. Heinze, Inc., Three Watson, Irvine, Calif. 92718-2767.

Operation of Pulsed Chromatic Light Source System

The only difference in operation between the chromatic source verses the monochromatic source is that the chromatic source requires excitation filter 25 to remove all the wavelengths of light, except a desired narrow excitation band. This allows the chromatic light source to function very similar to the monochromatic light source.

Figure 2A:
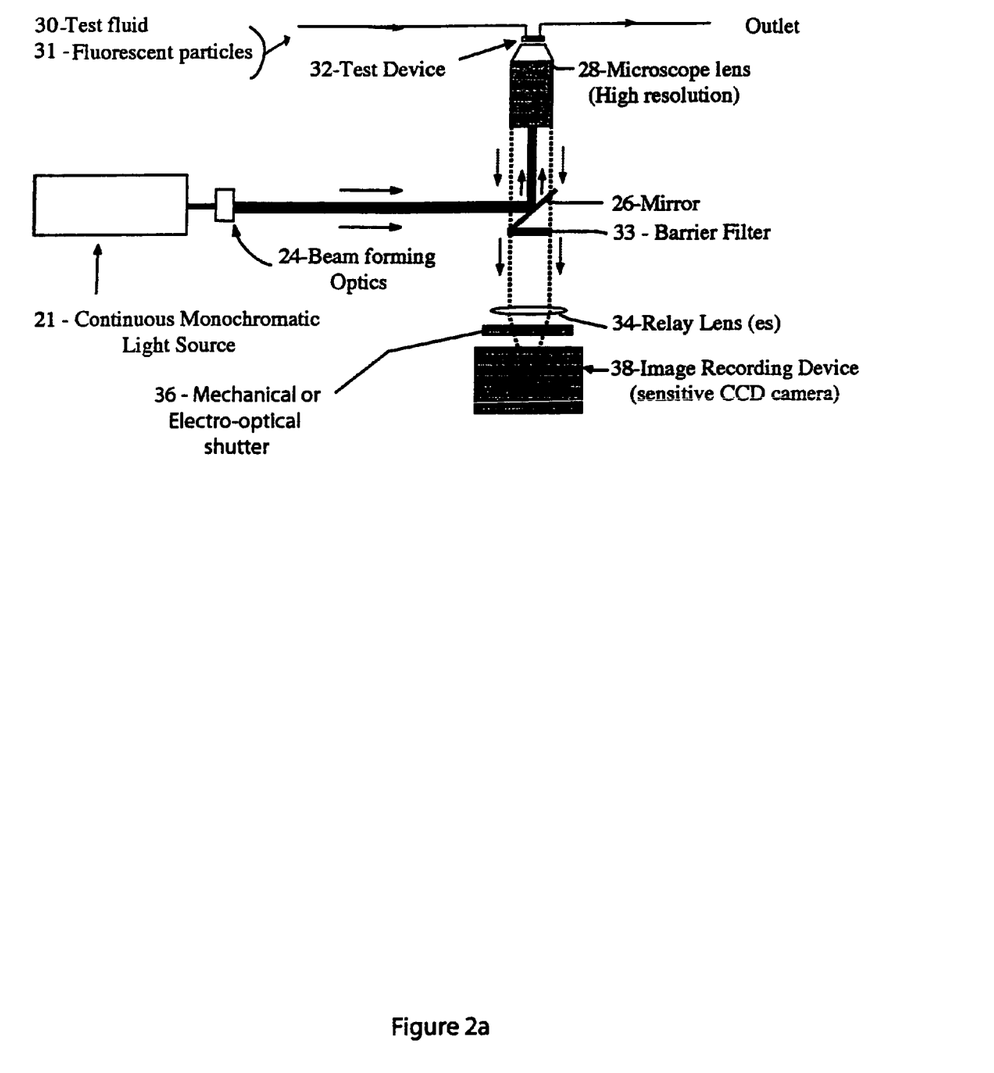
FIG. 2A. Schematic of a micro PIV system using a continuous monochromatic light source. The particle image field is shuttered by before the CCD camera.

FIG. 2A—Description of Continuous Monochromatic Light Source System

A third embodiment is shown in FIG. 2A. The major difference of this embodiment and the first two embodiments is that pulsed light source 19 or 20 is replaced by a continuous monochromatic light source 21. In practice continuous monochromatic light source 21 can be, but not restricted to, any continuous monochromatic laser, such as a He—Ne laser.

A shutter 36 is located between relay lens 34 and image recording device 38. The shutter can either be mechanical or electro-optical, and can be purchased through various optical supply catalogs, or as part of an image intensifier system for CCD cameras, from a CCD camera supplier such as Roper Scientific (formerly Princeton Instruments), 3660. Quakerbridge Rd., Trenton, N.J. 08619.

Operation of Continuous Monochromatic Light Source System

After the continuous monochromatic light source 21 passes through the beam-forming optics and is reflected by mirror 26, it is then passed through microscope lens 28, and enters test device 32. Fluorescent particles 31 continuously absorb the excitation light and continuously emit fluorescent light, which is imaged by microscope lens 28, transmitted through mirror 26, passed through barrier filter 33, and relay lens 34. Shutter 36 gates the continuous fluorescent light creating two or more exposures of the particle image field on image recording device 38. The combination of continuous light source 21 and shutter 36 function similarly to pulsed light source 19, with the exception that test device 32 and fluorescent particles 31 are continuously illuminated instead of pulse illuminated.

Figure 2B:
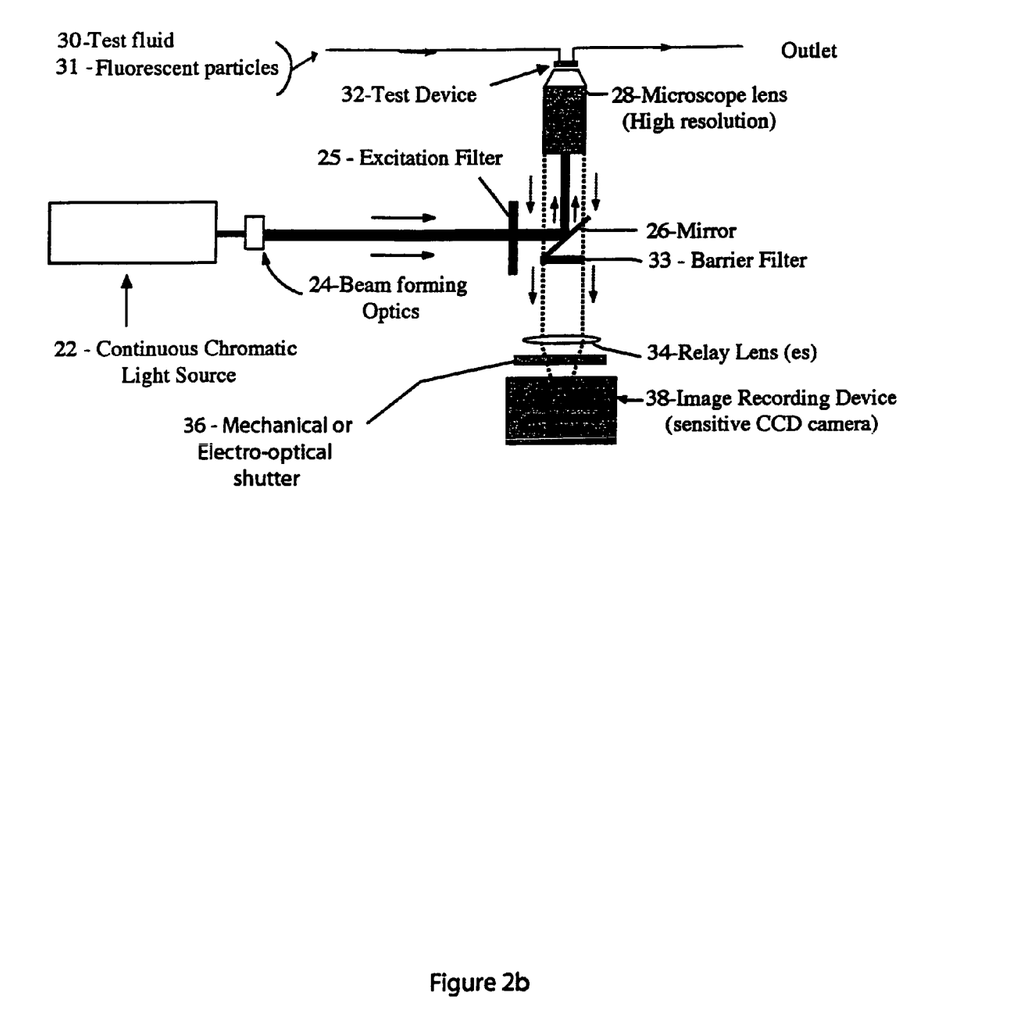
FIG. 2B. Schematic of a micro PIV system using a chromatic continuous light source. The particle image field is shuttered before the CCD camera.

FIG. 2B—Description of Continuous Chromatic Light Source System

FIG. 2B shows an embodiment when continuous monochromatic light source 21 is replaced by continuous chromatic light source 22, which can be but not limited to an Argon-Ion laser, a halogen lamp, or a Mercury-arc lamp. This embodiment was published in July of 1998 by Santiago Wereley, Meinhart, Adrian & Beebe (1998). Halogen and Mercury-arc lamps are standard illumination sources for microscopes and are available from A.G. Heinze, Inc., Three Watson, Irvine, Calif. 92718-2767. An excitation filter 25 is located between beam forming optics 24 and mirror 26. Excitation filters can be purchased from A.G. Heinze, Inc., Three Watson, Irvine, Calif. 92718-2767.

Operation Continuous Chromatic Light Source System

Since continuous chromatic light source 22 illuminates several wavelengths of light (i.e. chromatic illumination), excitation filter 25 is used to filter out all unwanted wavelengths of light, so that only the desired excitation wavelength of light reaches test device 32, and ultimately fluorescent particles 31.

After the continuous light passes through excitation filter 25, it is reflected by mirror 26, it is then passed through microscope lens 28, and enters test device 32. Fluorescent particles 31 continuously absorb the excitation light and continuously emit fluorescent light, which is imaged by microscope lens 28, transmitted through mirror 26, passed through barrier filter 33, and relay lens 34. Shutter 36 gates the continuous fluorescent light creating two or more exposures of the particle image field on image recording device 38.

Figure 3A:
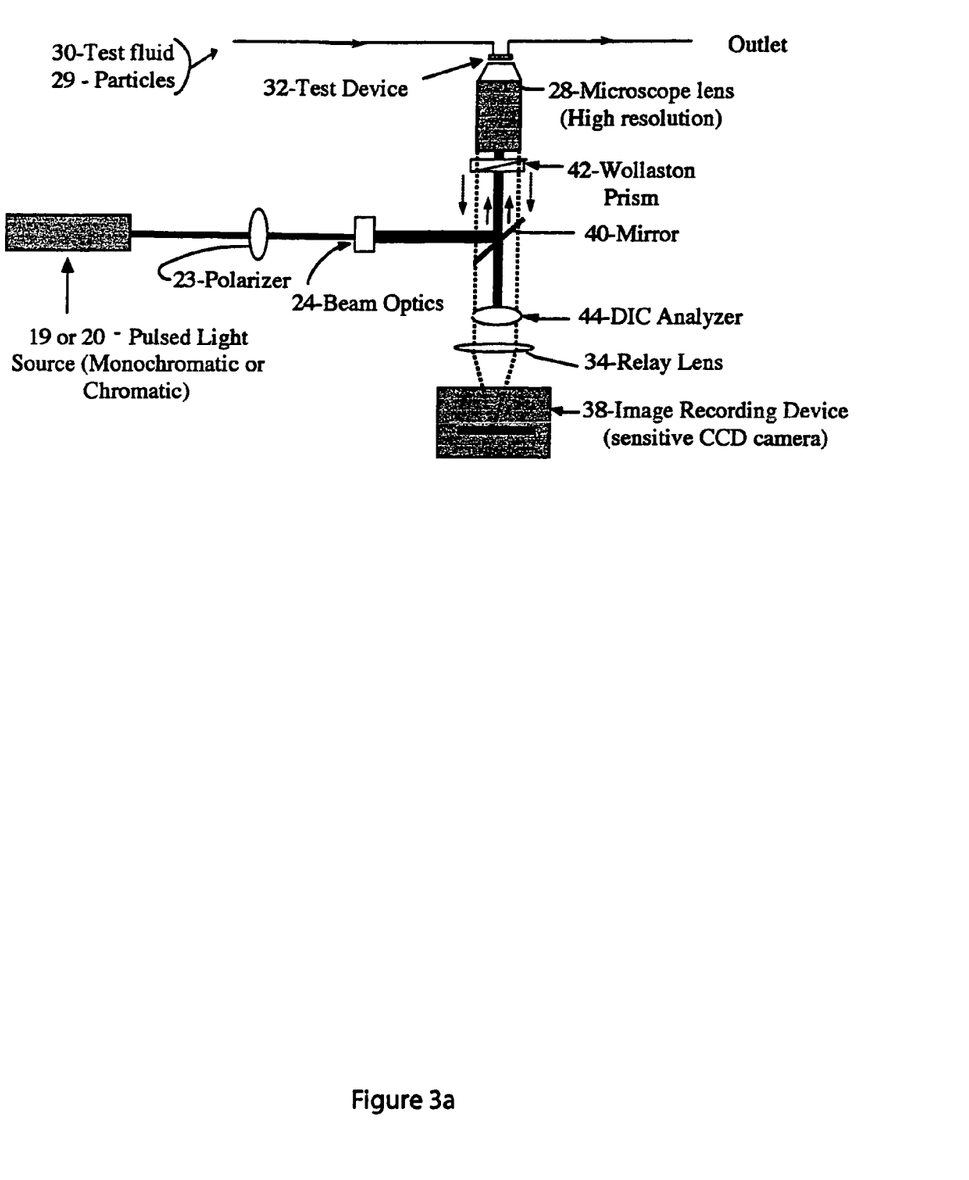
FIG. 3A. Schematic of a micron-resolution PIV system using reflective Differential Interference Contrast using a pulsed light source.

FIG. 3A—Description of Differntial Interferenc Contrast (DIC) System with Pulsed Light Sourc The fifth embodiment is shown in FIG. 3A. It uses differential interference contrast (DIC) imaging instead of epi-fluorescence imaging to record the images of particles, which are both standard microscope techniques. This embodiment uses monochromatic pulsed light 19 or chromatic pulsed light source 20. Since epi-fluorescence imaging is not used, it is not so important to distinguish between monochromatic and chromatic light sources.

The main difference between the DIC embodiment and the previous four embodiments is that excitation filter 25, barrier filter 33, and mirror 26 are replaced by a polarizer 23, mirror 40, Wollaston prism 42, and DIC analyzer 44. Polarizer 23 is oriented vertically (for the current configuration), and is located after the light source 20 or 22, and before Wollaston prism 42. In FIG. 3A, polarizer 23 is located before beam optics 24, but it could be placed equivalently after beam optics 24 and before mirror 40. Mirror 40 is a half-silvered mirror, which has no anti-reflective coating. DIC analyzer 44 is placed before relay lens 34, but could be placed equivalently after relay lens 34 but before image recording device 38. The polarizer, Wollaston prism, and DIC analyzer are available at microscope suppliers such as A.G. Heinze, Inc., Three Watson, Irvine, Calif. 92718-2767.

Operation of Differential Interference Contrast System with Pulsed Light Source

Light is emitted from pulsed light source 19 or 20. Polarizer 23 is orientated vertically so that only vertically polarized light is passed. If the light from pulsed light source 19 or 20 is already vertically polarized, polarizer 23 is not required. The linearly polarized light is reflected by mirror 40, and passed to Wollaston prism 42.

The Wollaston prism is a birefringent prism that shears the linearly polarized light (i.e. the linear polarized light is divided into two orthogonal components of polarization, and one component is displaced a small amount (~50–200 nm) relative to the other component). The two polarized components are passed through microscope lens 28 and enter test device 32. If one of the components is reflected on the surface of the test device while the other component is reflected by some obstruction such as a particle 29 or 31, then the two components will have a phase shift or amplitude change relative to each other. If there is a phase shift or amplitude change between the two reflected components they recover a different polarization when they pass back through Wollaston prism 42. In contrast, the non-disturbed components will recover the initial polarization when transmitted back through Wollaston prism 42. The reflected light is then passed through mirror 40 and reaches DIC analyzer 44. DIC analyzer 44 consists of a linear polarizer, which is oriented in the cross direction to polarizer 23. The only light that passes through the DIC analyzer is light associated with an obstruction in the test device which has feature sizes of the same size as the beam shear produced by the Wollaston prism, such as particle 29.

The reflective DIC technique allows image recording device 38 to record images of light scattered from the sub-micron particles without the aid of fluorescence. Reflective DIC is a standard microscope technique, but has never been applied to Particle Image Velocimetry (PIV). For more information on DIC, consult Inoue & Spring (1997).

Figure 3B:
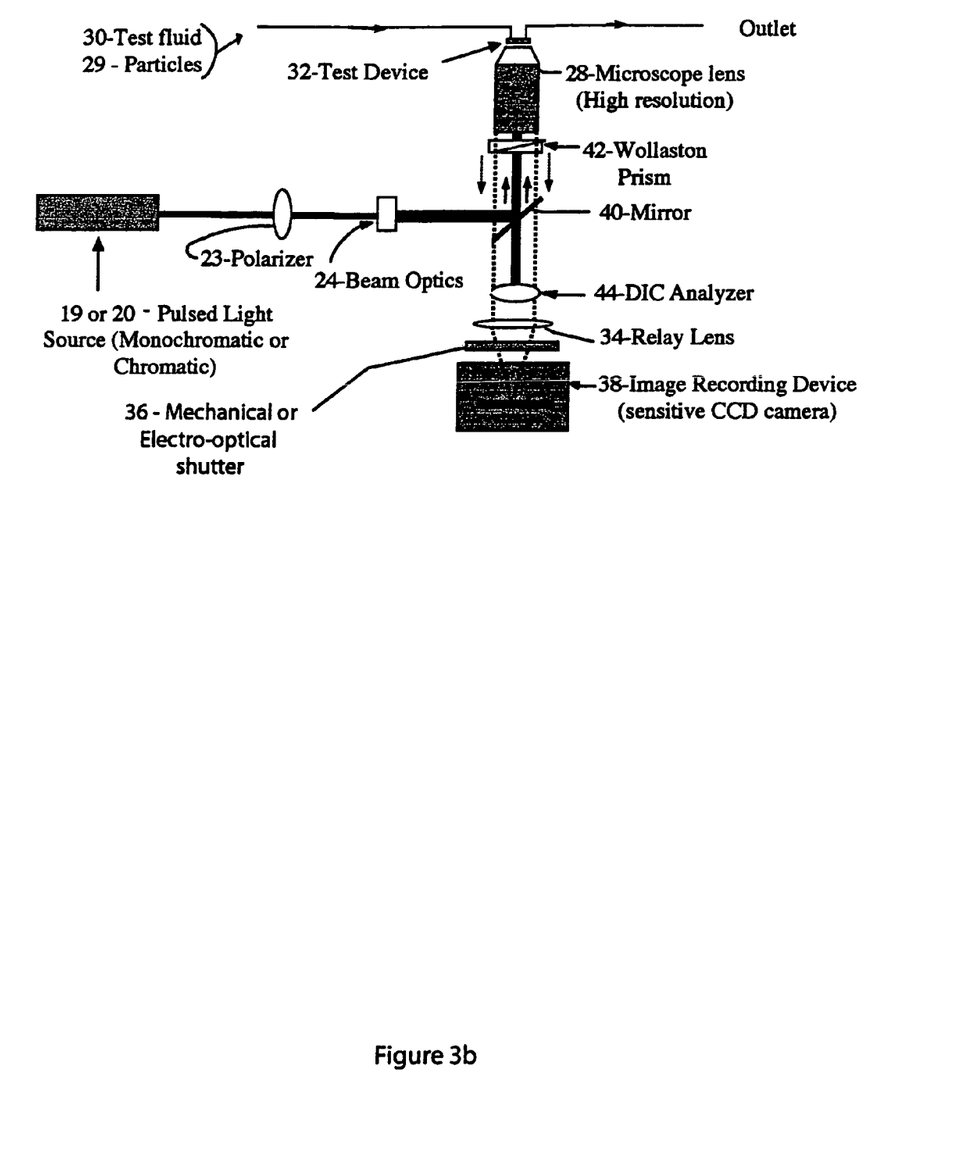
FIG. 3B. Schematic of a micron-resolution PIV system using reflective Differential Interference Contrast and a continuous light source.

FIG. 3B—Description of Differential Interference Contrast (DIC) System with Continuous Light Source FIG. 3B shows an embodiment when continuous light source 21 or 22 (monochromatic or chromatic) is used instead of pulsed light source 19 or 20. Shutter 36 is located between relay lens 34 and image recording device 38. Shutter 36 can be place at any convenient point throughout the optical path, provided that it does not interfere with the imaging system.

Operation of Differential Interferenc Contrast (DIC) System with Continuous Light Source After the continuous light passes through the DIC system, it is gated by shutter 36 to control the exposure of the particle image field on image recording device 38.

Figure 4:
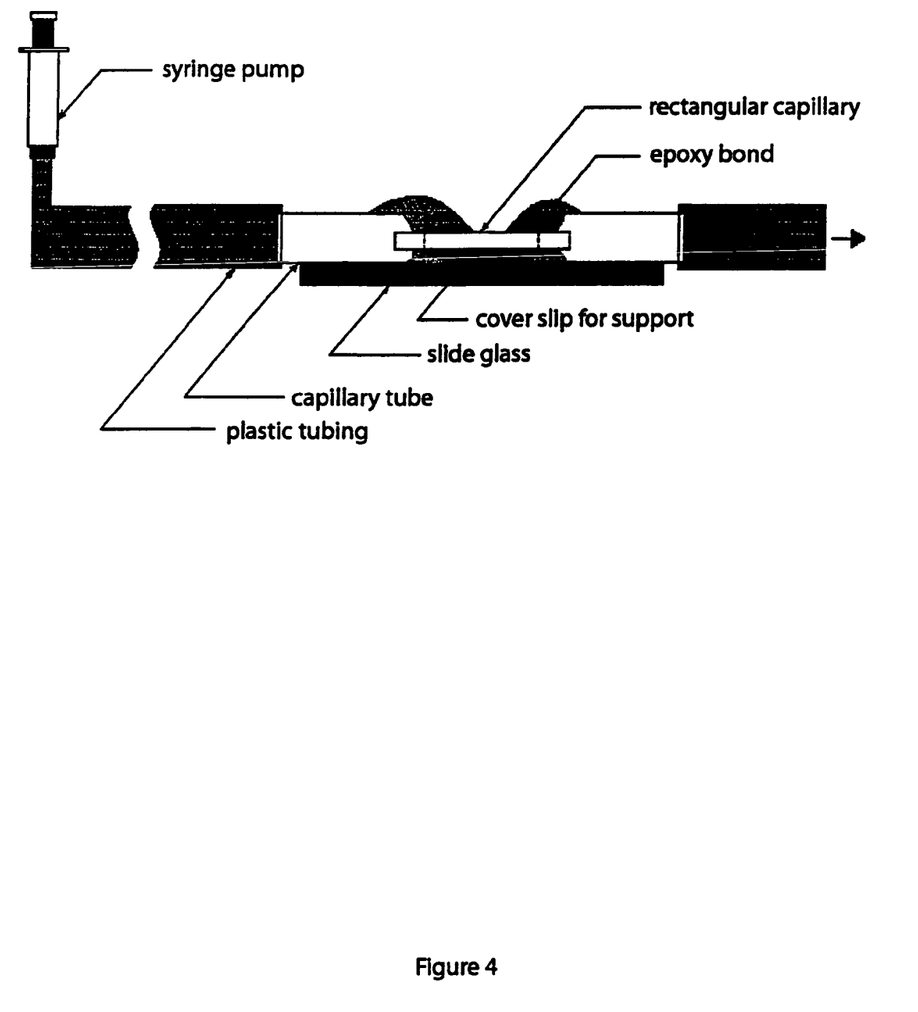
FIG. 4. Detail of the nominally 30 mm×300 mm rectangular glass microchannel, which is glued to a circular capillary tube and a 170 mm glass coverslip for support. Plastic tubing connects the capillary tube to the syringe pump.
Figure 5A:
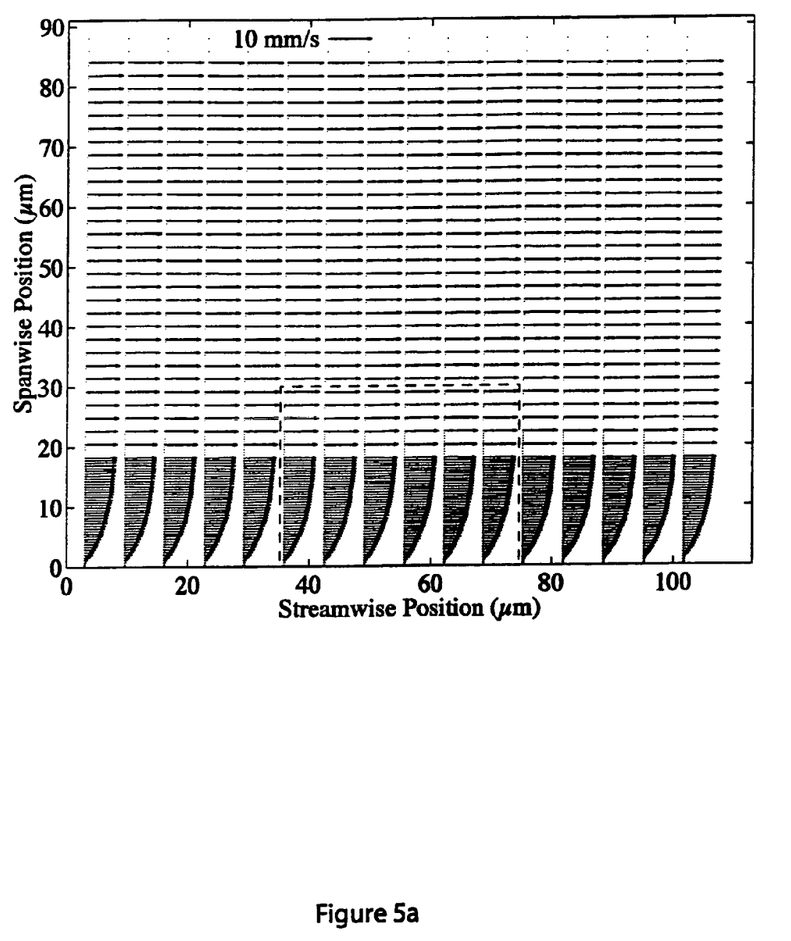
FIG. 5A. Ensemble-averaged 100 µm×85 µm velocity-vector field measured in a 30 mm deep×300 mm wide×25 mm channel. The spatial resolution, defined by the interrogation spot size of the first interrogation window, is 13.6 µm×4.4 µm away from the wall, and 13.6 µm×0.9 µm near the wall. A 50% overlap between interrogation spots yields a velocity vector spacing of 450 nm in the wall-normal direction near the wall.
Figure 5B:
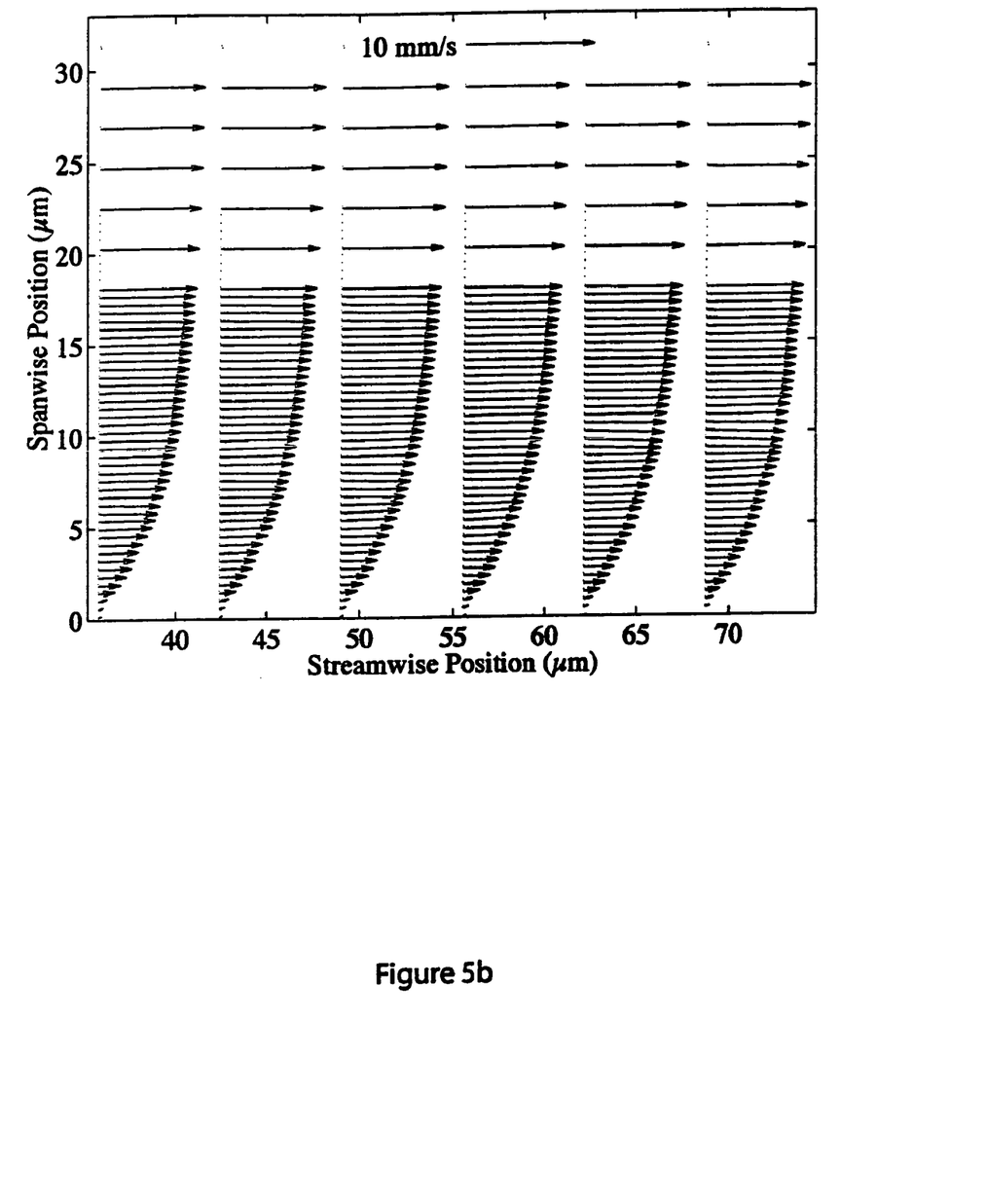
FIG. 5B. Ensemble-averaged 30 µm×30 µm velocity-vector field measured in a 30 mm deep×300 mm wide×25 mm channel. The spatial resolution, defined by the interrogation spot size of the first interrogation window, is 13.6 µm×4.4 µm away from the wall, and 13.6 µm×0.9 µm near the wall. A 50% overlap between interrogation spots yields a velocity vector spacing of 450 nm in the wall-normal direction near the wall.
Figure 6:
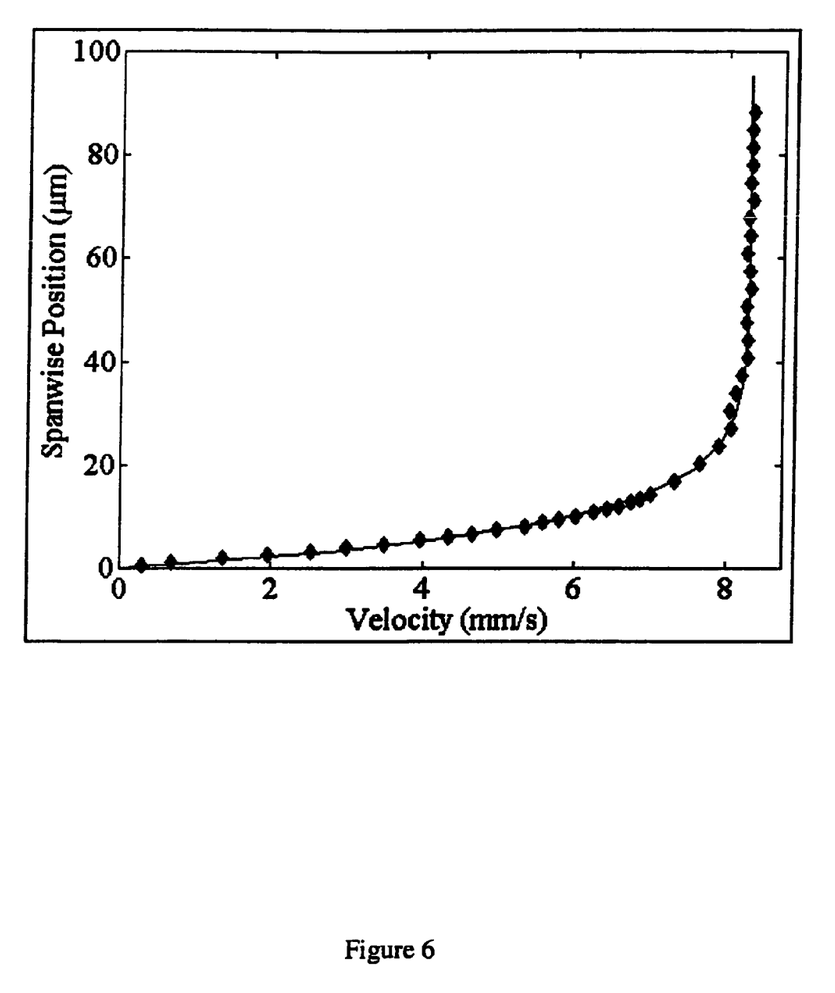
FIG. 6. Ensemble-averaged velocity profile measured in a nominally 30 mm×300 mm channel. The symbols represent ensemble-averaged and streamwise-averaged PIV data. The solid line is the analytical solution for Newtonian flow through a rectangular channel.
Figure 7:
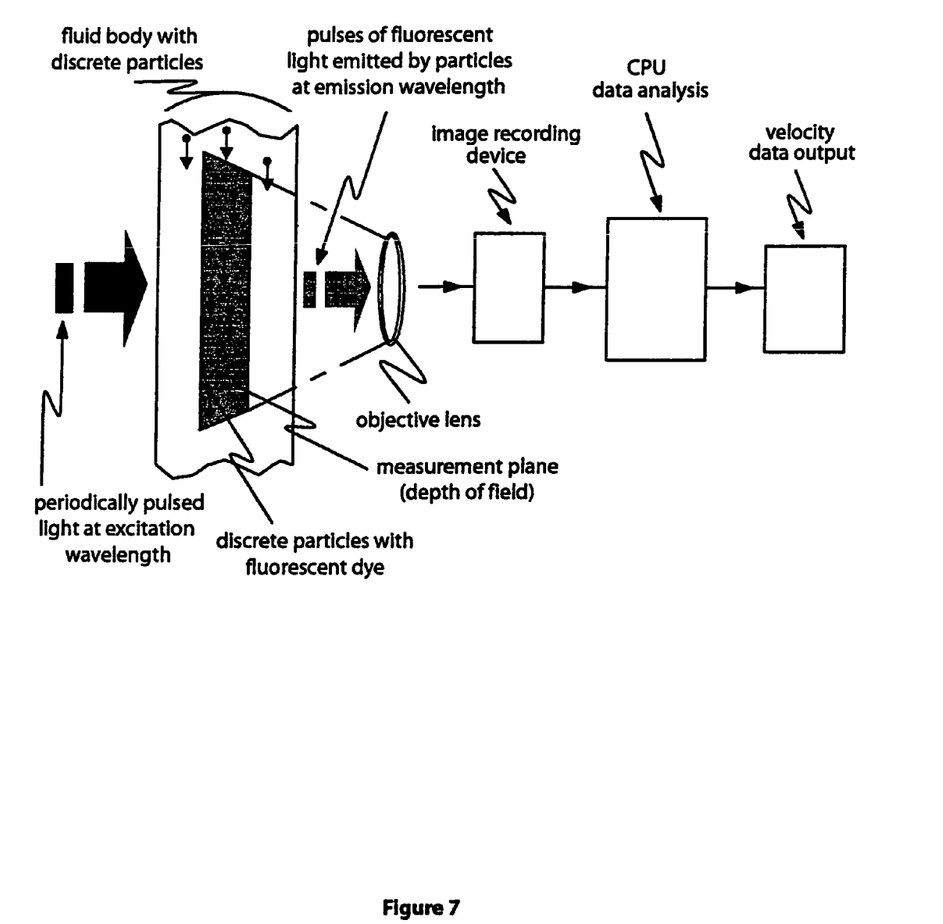
FIG. 7. Schematically illustrates the measurement method of the present invention.

FIGS. 4–6 Demonstration of Velocimetry in a Microchannel Flow

A demonstration experiment was conducted using the first embodiment of the invention shown in FIG. 1A. The velocity measurements demonstrate several objects and advantages of the invention. In this experiment, we obtained sub-micron spatial resolutions of 0.9 μm on regularly spaced grids, and velocity measurements within 450 nm of a surface. By changing the time between exposures, velocities ranging from 50 microns per second to 300 meters per second can be obtained. The velocity measurements are shown to be accurate to within 2% full scale resolution.

A 30 μm×300 μm×25 mm glass rectangular microchannel, fabricated by Wilmad Industries, was mounted flush to a 170 μm thick glass coverslip and a microscope slide (see FIG. 4). By carefully rotating the glass coverslip and the CCD camera, the channel was oriented to the optical plane of the microscope within 0.20, in all three angles. The orientation was confirmed optically by focusing the CCD camera on the microchannel walls. The microchannel was horizontally positioned using a high-precision x-y stage, and verified optically to within ~400 nm using epi-fluorescent imaging and image enhancement.

The glass microchannel was imaged using epi-fluorescent system shown in FIG. 1A. A Nikon Plan Apochromat oil-immersion objective lens with a magnification M=60 and a numerical aperture NA=1.4 was used to image the particles. The object plane was at approximately 7.5±1 microns from the bottom of the 30 micron thick microchannel. The Plan Apochromat lens was chosen for the experiment, because it is a high quality microscope objective designed with low curvature of field, low distortion, and corrected for spherical and chromatic aberrations (Inoué & Spring, 1997).

Using a microscope lens with a magnification M=60, a numerical aperture of NA=1.4, and a flow-tracing particle diameter with diameter of 200 nm, the effective particle image diameter projected onto the CCD camera sensor will be 31.7 μm (see Meinhart, Wereley & Santiago, 1999a). The effective particle diameter when projected back into the flow is 528 nm. If a particle image diameter is resolved by 3–4 pixels, the location of a particle-image correlation peak can be determined to within $1/10^{th}$ the particle-image diameter. For the parameters consider here, the uncertainty reduces to 52.8 nm.

The fact that one can measure particle displacement to within 53 nm is somewhat surprising. In most microscopic applications, one is primarily interested in determining the shape of small objects. Obviously, the smallest resolvable shape is on the order of the resolution of the microscope. In micro PIV, one knows a priori the particle shape and is interested only in determining particle position. By oversampling the image (i.e. resolving the image with 3–4 pixels across the image diameter), one can determine particle position to within an order of magnitude better resolution than the diffraction-limited resolution of the microscope.

The ability to resolve a particle's location to within 52.8 nm is the key that allows this system to make high-resolution measurements on the order of one micron. Obviously, if one tracks the velocity of a single particle by observing two exposures, the distance between successive exposures would only have to be on the order of a few microns to make an accurate velocity measurements.

Since deionized water was used as the working fluid, the effective numerical aperture of the objective lens was limited to NA≈1.23. A filtered continuous white light source (see FIG. 2B) was used to align the test section with the CCD camera and to test for proper particle concentration. During the experiment, the continuous light source was replaced by the pulsed Nd:YAG laser. A Harvard Apparatus syringe pump was used to produce a 200 μl hr$^{-1}$ flow through the microchannel.

The particle-image fields were analyzed using a PIV interrogation program published in July 1998 by Meinhart, Wereley & Santiago (1999b). The algorithm uses an averaging correlation technique to estimate velocity vectors at a single measurement points by (1) cross correlating particle-image fields from twenty instantaneous realizations, (2) averaging the cross correlation functions, and (3) determining the peak of the average correlation function. This process is repeated for each velocity vector in the measurement domain. The signal-to-noise ratio is significantly increased by ensemble averaging the correlation function before peak detection, as opposed to either ensemble averaging the velocity vectors after peak detection, or ensemble averaging the particle-image field before correlation. The average correlation technique is limited to steady or periodic flows. For the current experiment, twenty realizations were chosen because that was more than a sufficient number of realizations to give excellent signal, even with a first interrogation window of only 120×8 pixels.

The signal-to-noise ratio resulting from the ensemble-average correlation technique was high enough that there were no erroneous velocity measurements. Consequently, no vector validation was performed on the data after interrogation. The velocity field was smoothed using a 3×3 Gaussian kernel with a standard deviation of 1 grid spacing in both directions.

FIGS. 5A & 5B show an ensemble-averaged velocity-vector field of the microchannel. The images were analyzed using a low spatial resolution away from the wall, where the velocity gradient is low, and using a high spatial resolution near the wall, where the wall-normal velocity gradient is largest. The interrogation spots were chosen to be longer in the streamwise direction than in the wall-normal direction. This allowed for a sufficient number of particle images to be captured in an interrogation spot, while providing the maximum possible spatial resolution in the wall-normal direction. The spatial resolution, defined by the size of the first interrogation window was 120×40 pixels in the region far from the wall, and 120×8 pixels near the wall. This corresponds to a spatial resolution of 13.6 mm×4.4 mm and 13.6 mm×0.9 mm, respectively. The interrogation spots were overlapped by 50% to satisfy the Nyquist sampling criterion. Consequently, the velocity-vector spacing in the wall-normal direction was 450 nm near the wall. The streamwise velocity profile was estimated by line-averaging the measured velocity data in the streamwise direction. FIG. 6 compares the streamwise velocity profile estimated from the PIV measurements (shown as symbols) to the analytical solution for laminar Newtonian flow in a rectangular channel (shown as a solid line). The agreement is within 2% full-scale resolution. The bulk flow rate of the analytical curve was determined by matching the free-stream velocity data away from the wall. The wall position of the analytical curve was determined by extrapolating the velocity profile to zero near the wall.

Conclusions, Ramifications, and Scope

Accordingly, the reader will see that the micron-resolution particle image velocimetry system depicted here is a practical system for measuring velocity fields with spatial resolutions approaching one micron and temporal resolutions approaching tens of nanoseconds. The velocity data can be measured simultaneously at thousands of points on regularly spaced grid points, to give an overall picture of the flow field. In addition, the measurements are accurate to within 2% full-scale resolution. Using the fluorescence technique, background reflections from the walls can be filtered out so that velocity measurements can be made within 450 nm of the wall. The differential interference contrast (DIC) technique can be used to image sub-micron particles without the aid of fluorescence.

Although the description above contains many specificities, these should not be construed as limiting the scope of the invention but as merely providing illustrations of some of the presently preferred embodiments of this invention.

The test device is usually a planar device such as a Hele-Shaw flow cell, a micro-electromechanical system (such as a silicon micromachined devices with transparent wafers), biological materials, or possibly even a wind tunnel.

The microscope lens can be any lens with sufficient magnification and resolving power to image the desire particle images. The lens could be either an air immersion, oil immersion, or water immersion. There can be any number of lenses that relay light from the particles to the recording device.

The image recording device can consist of a variety of electronic or photometric devices that are sensitive enough to record the images with the desired duration of exposure, which may include a standard CCD camera, back-thinned illuminated CCD cameras, intensified camera, or even photographic film.

While most of the velocity measurements are usually obtained using two particle image exposures, measurements can be obtained in principle using multiple particle image exposures.

In addition, phase contrast imaging or amplitude contrast imaging could potentially be used instead of differential interference contrast (DIC); higher quality images may be obtained by using incoherent light sources; infrared or ultraviolet wavelengths may be used to image through devices that are non-transparent to visible light; epi-fluorescence illumination is preferred but other types of illumination such as direct illumination of the test device may be suitable. Direct illumination of the test device using a delivery such as a fiber optic may be used instead of epi-illumination. Thus, the scope of the invention should be determined by the appended claims and their legal equivalents, rather than by the examples given.

We claim:

1. A method of measuring motion within a fluid body comprising the steps of:
   (a) injecting a plurality of solid particles into the fluid body in dispersed relation to move therewith;
   (b) applying a short pulse of light through an objective lens to the fluid body so as to broadly illuminate the fluid body, and then repeating the application of the light pulse after a known time delay;
   (c) after each pulse of the applied light, observing through the same objective lens the light scattered from the individual solid particles;
   (d) wherein only light from the solid particles lying within the depth of field of the objective lens will produce well-focused discrete images of discrete particles, thereby determining a two-dimensional measurement plane in the flowing fluid; and
   (e) comparing discrete images of discrete particles successively observed in the measurement plane as a function of time to determine the motion of the fluid body.

2. The method of claim 1 wherein an image recording device is positioned to receive light transmitted from the test device through the objective lens for recording discrete images of discrete particles.

3. The method of claim 1 wherein the images of discrete particles are observed to determine two vectorial components of the measurement field.

4. The method of claim 1 wherein the wavelength of the light lies within the range of ultraviolet to infrared.

5. The method of claim 4 wherein the wavelength of the light is within the ultraviolet range.

6. The method of claim 4 wherein the wavelength of the light is within the infrared range.

7. The method of claim 4 wherein the wavelength of the light is within the visible range.

8. The method of claim 1 wherein the light pulses are applied at periodic intervals and the comparison is accomplished by analyzing a successively recorded time sequence of discrete images of discrete particles by average correlation analysis at multiple points within the image field to determine the average fluid velocities of multiple respective points within the two-dimensional measurement plane.

9. The method of claim 8 wherein the images of discrete particles are observed to determine two vectorial components of the measurement field.

10. The method of claim 1 wherein the light pulses are applied to a half-silvered mirror, and are reflected from the mirror into the fluid body.

11. The method of claim 10 wherein an image recording device is positioned to receive light transmitted from the test device through the objective lens and the mirror, for recording discrete images of discrete particles.

12. A method of measuring motion within a fluid body comprising the steps of:
   (a) injecting a plurality of solid particles into the fluid body in dispersed relation to move therewith;
   (b) periodically applying short pulses of light with a known time separation to a mirror so as to be reflected from the mirror through an objective lens into the fluid body so as to then broadly illuminate the fluid body;
   (c) after each applied pulse of light, observing through the same objective lens the light scattered from the individual solid particles, whereby only light from the solid particles lying within the depth of field of the objective lens will produce well-focused discrete images of discrete particles, thereby determining a two-dimensional measurement plane in the flowing fluid; and
   (d) then comparing successively observed discrete images of discrete particles as a function of time to determine the motion of the fluid body.

13. The method of claim 12 wherein an image recording device is positioned to receive scattered light transmitted through the objective lens for recording discrete images of discrete particles.

14. The method of claim 13 wherein the images of discrete particles are observed to determine two vectorial components of the measurement field.

15. The method of claim 12 wherein the wavelength of the light lies within the range of ultraviolet to infrared.

16. The method of claim 15 wherein the wavelength of the light is within the ultraviolet range.

17. The method of claim 15 wherein the wavelength of the light is within the infrared range.

18. The method of claim 15 wherein the wavelength of the light is within the visible range.

19. The method of claim 12 wherein the comparison is accomplished by analyzing a successively recorded time sequence of discrete images of discrete particles by average correlation analysis at multiple points within the image field to determine the average fluid velocities of multiple respective points within a two-dimensional measurement plane.

20. The method of claim 19 wherein the images of discrete particles are observed to determine two vectorial components of fluid velocity.

21. The method of claim 12 wherein the duration of the pulses of light is of the order of five nanoseconds, and the known time separation between pulses is in the approximate range of several nanoseconds to several seconds.

22. A method of measuring with approximately microscale spatial resolution the velocity of a flowing fluid, the method comprising the steps of:
   (a) injecting into the fluid a plurality of solid particles that approximately follow the motion of the flowing fluid,
   (b) selecting a light source for repetitively delivering closely spaced pulses of light having a known duration of the order of five nanoseconds, and a known time delay between the spaced pulses in the approximate range of several nanoseconds to several a seconds;
   (c) positioning a microscope objective lens having a known depth of field to transmit pulses of light from the light source into the flowing fluid and positioned to image within the flowing fluid;
   (d) gathering pulses of light, scattered by the solid particles contained within the flowing fluid, through the same microscope objective lens;
   (e) relaying the gathered pulses of light from the objective lens to an image recording device, thereby recording discrete images of discrete particles;
   (f) wherein only light from the solid particles lying within the depth of field of the objective lens will produce well-focused discrete images of discrete particles that are recorded by the image recording device, thereby determining a two-dimensional measurement plane in the flowing fluid; and
   (g) which further includes the step of analyzing a successively recorded time sequence of discrete images of discrete particles by average correlation analysis at multiple points within the image field to determine the average fluid velocities at multiple respective points within the two-dimensional measurement plane.

23. The method of claim 22 wherein the wavelength of the light lies within the range of ultraviolet to infrared.

24. The method of claim 23 wherein the wavelength of the light is within the ultraviolet range.

25. The method of claim 23 wherein the wavelength of the light is within the infrared range.

26. The method of claim 23 wherein the wavelength of the light is within the visible range.

* * * * *